(12) United States Patent
Moriguchi et al.

(10) Patent No.: US 6,569,303 B1
(45) Date of Patent: May 27, 2003

(54) METHOD OF ADJUSTING OUTPUT OF GAS SENSOR

(75) Inventors: Keigo Moriguchi, Takahama (JP); Makoto Nakae, Toyoake (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/663,345

(22) Filed: Sep. 15, 2000

(30) Foreign Application Priority Data

Sep. 17, 1999 (JP) .......................................... 11-264192
Aug. 1, 2000 (JP) ...................................... 2000-233596

(51) Int. Cl.⁷ .......................................... G01N 27/407
(52) U.S. Cl. ........................ 204/426; 204/427; 204/429
(58) Field of Search ................................. 204/421–429

(56) References Cited

U.S. PATENT DOCUMENTS 4,883,643 A * 11/1989 Nishio et al.
5,310,472 A * 5/1994 Dietz et al.
5,685,964 A    11/1997 Watanabe et al.

FOREIGN PATENT DOCUMENTS

JP    7-27391    6/1995
JP    8-193974   7/1996

* cited by examiner

*Primary Examiner*—T. Tung
(74) *Attorney, Agent, or Firm*—Nixon & Vanderhy P.C.

(57) ABSTRACT

A method of adjusting an output of a gas sensor element is provided. The gas sensor element includes a lamination of a solid electrolyte body, a target gas-exposed electrode, a reference gas-exposed electrode, and a diffused resistance layer in which a target gas to be measured diffuses. The target gas-exposed electrode is disposed on a first surface of the solid electrolyte body exposed to the target gas. The reference gas-exposed electrode is disposed on a second surface of the solid electrolyte body exposed to a reference gas. The diffused resistance layer is disposed on the first surface of the solid electrolyte body. The target gas-exposed electrode and the reference gas-exposed electrode produce a sensor output. The adjustment of the sensor output is achieved by decreasing a diffusion length of the target gas in the diffused resistance layer as a function of a quantity of the sensor output to be adjusted by, for example, removing a portion of the diffused resistance layer.

6 Claims, 11 Drawing Sheets

METHOD OF ADJUSTING OUTPUT OF GAS SENSOR

BACKGROUND OF THE INVENTION

1. Technical Field of the Invention

The present invention relates generally to a method of adjusting an output of a gas sensor element which may be employed in air-fuel ratio control for an internal combustion engine of automotive vehicles.

2. Background Art

A typical gas sensor element employed in the air-fuel ratio control for automotive vehicles includes a solid electrolyte body made of an oxygen ion conductive material, a gas measuring and a reference gas-exposed electrode, and a diffused resistance layer. The diffused resistance layer is disposed on a surface of the target gas-exposed electrode exposed to a target gas to be measured. The target gas, thus, reaches the target gas-exposed electrode through the diffused resistance layer.

When the voltage is applied to the target gas-exposed electrode and the reference gas-exposed electrode, the current flowing through these electrodes is determined as a function of the number of oxygen molecules passing through the diffused resistance layer. The current flowing through the electrodes, thus, shows characteristics that it is saturated at a given value as long as the concentration of oxygen in a target gas is constant.

FIG. 16 represents the relation between the voltage applied to the target gas-exposed electrode and the reference gas-exposed electrode and the current output picked up from the electrodes for difference concentrations a to d of oxygen (a>b>c>d). The drawing shows that application of a suitable voltage, for example, voltage V to the target gas-exposed electrode and the reference gas-exposed electrode causes the current to flow through the electrodes as a function of the concentration of oxygen. For instance, when the concentration of oxygen is a, the current Ia flows through the electrodes. This is the principle of measurement of the concentration of oxygen in the above gas sensor element.

However, when the above type of gas sensor elements are mass-produced, they may have a unit-to-unit variation in the above described characteristics. If there is no unit-to-unit variation, the application of voltage to the target gas-exposed electrode and the reference gas-exposed electrode of each gas sensor element exposed to a target gas whose concentration of oxygen is a will cause the current Ia to be, as shown in FIG. 16, produced by the electrodes. If, however, there is the unit-to-unit variation, the currents produced by the gas sensor elements show the distribution, as shown in FIG. 17. Some of the gas sensor elements producing the currents outside the range ΔIa will produce great measurement errors that are objectionable in practical use.

In order to eliminate the unit-to-unit variation of the gas sensor elements caused by production errors, Japanese Utility Model Second Publication No. 7-27391 teaches use of a correction circuit which corrects the output current of each gas sensor element. This method, however, results in complexity of the whole circuit structure of gas sensors and an increase in manufacturing cost.

SUMMARY OF THE INVENTION

It is therefore a principal object of the present invention to avoid the disadvantages of the prior art.

It is another object of the present invention to provide a simple and low-cost adjusting method of adjusting an output of a gas sensor.

According to one aspect of the invention, there is provided a gas sensor output adjusting method of adjusting a sensor output of a gas sensor element. The gas sensor element includes a lamination of a solid electrolyte body, a target gas-exposed electrode, a reference gas-exposed electrode, and a diffused resistance layer in which a target gas to be measured diffuses. The target gas-exposed electrode is disposed on a first surface of the solid electrolyte body exposed to the target gas. The reference gas-exposed electrode is disposed on a second surface of the solid electrolyte body exposed to a reference gas. The diffused resistance layer is disposed on the first surface of the solid electrolyte body. The target gas-exposed electrode and the reference gas-exposed electrode produce the sensor output. The adjustment of the sensor output is achieved by decreasing a diffusion length of the target gas in the diffused resistance layer as a function of a quantity of the sensor output to be adjusted.

In the preferred mode of the invention, the decreasing the diffusion length is achieved by removing a portion of the diffused resistance layer.

The diffused resistance layer includes a porous layer and a dense layer. The decreasing the diffusion length may be achieved by removing a portion of the porous layer.

The diffused resistance layer may include only the porous layer.

The decreasing the diffusion length may alternatively be achieved by removing a portion of the dense layer so as to broaden an area of the porous layer exposed to the target gas.

According to the second aspect of the invention, there is provided a gas sensor output adjusting method of adjusting a sensor output of a gas sensor element. The gas sensor element includes a lamination of a solid electrolyte body, a target gas-exposed electrode, a reference gas-exposed electrode, and a diffused resistance layer in which a target gas to be measured diffuses. The target gas-exposed electrode is disposed on a first surface of the solid electrolyte body exposed to the target gas. The reference gas-exposed electrode is disposed on a second surface of the solid electrolyte body exposed to a reference gas. The diffused resistance layer is disposed on the first surface of the solid electrolyte body. The target gas-exposed electrode and the reference gas-exposed electrode produce the sensor output. The adjustment of the sensor output is achieved by decreasing a gas-diffusing sectional area of the diffused resistance layer within which the target gas diffuses as a function of a quantity of the sensor output to be adjusted.

In the preferred mode of the invention, the diffused resistance layer includes a porous layer and a dense layer. The decreasing the gas-diffusing sectional area of the diffused resistance layer is achieved by partially sealing a surface of the porous layer exposed to the target gas.

The decreasing the gas-diffusing sectional area of the diffused resistance layer may alternatively be achieved by forming a plurality of output-adjusting holes in the dense layer which lead to the porous layer and sealing a given number of the output-adjusting holes as a function of the quantity of the sensor output to be adjusted.

According to the third aspect of the invention, there is provided a gas sensor output adjusting method of adjusting a sensor output of a gas sensor element. The gas sensor element includes a lamination of a solid electrolyte body, a target gas-exposed electrode, a reference gas-exposed electrode, and a diffused resistance layer in which a target gas to be measured diffuses. The target gas-exposed electrode is disposed on a first surface of the solid electrolyte body exposed to the target gas. The reference gas-exposed electrode is disposed on a second surface of the solid electrolyte body exposed to a reference gas. The diffused resistance layer having an outer surface exposed to the target gas, an inner surface opposite the outer surface, disposed on the first surface of the solid electrolyte body, and side surfaces formed between the outer and inner surfaces, defining portions of side surfaces of the lamination. The target gas-exposed electrode and the reference gas-exposed electrode produce the sensor output. The adjustment of the sensor output is achieved by decreasing a diffusion length of the target gas in the diffused resistance layer as a function of a quantity of the sensor output to be adjusted by removing a portion of the diffused resistance layer obliquely to at least one of the side surfaces of the lamination.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1A:
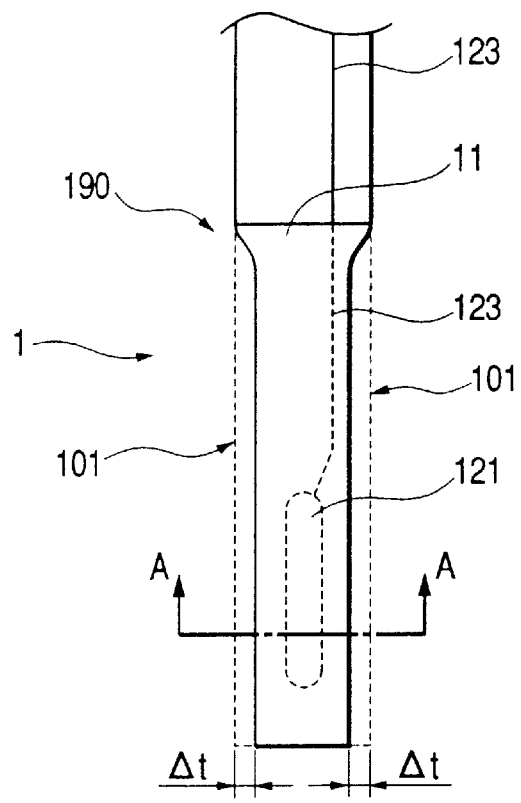
FIG. 1(a) is a partially plan view which shows a gas sensor element whose output is adjusted by a method according to the present invention.
Figure 1B:
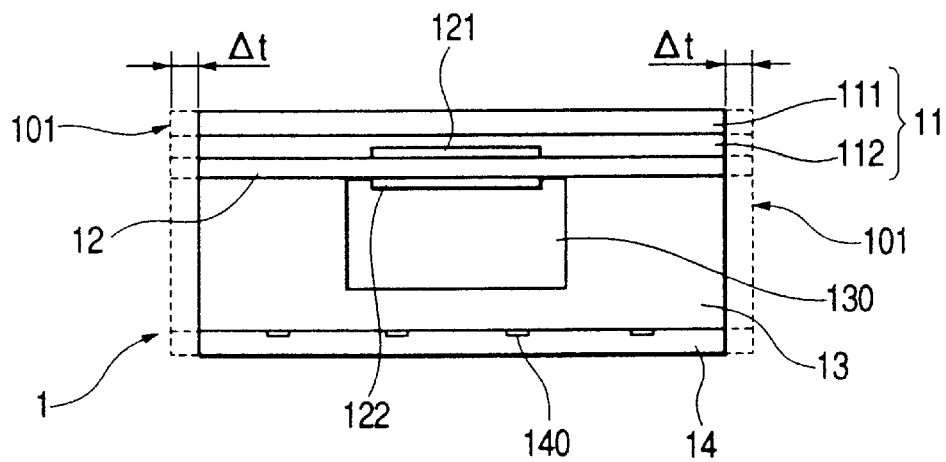
FIG. 1(b) is a vertical sectional view of FIG. 1(a)

Referring now to the drawings, wherein like numbers refer to like parts in several views, particularly to FIGS. 1(a) and 1(b), there is shown a gas sensor whose output is controlled by an output adjusting method according to the present invention.

The gas sensor may be used with an automotive control system designed to control the quantity of fuel injected into an internal combustion engine as a function of the concentration of gas such as oxygen or nitrogen oxide contained in exhaust gasses measured by the gas sensor under feedback control to bring the air-fuel ratio into agreement with a target one. The gas sensor may also be designed to measure the concentration of CO or HC.

The gas sensor includes a gas sensor element 1 which, as shown in FIGS. 1(a) and 1(b), consists of a solid electrolyte body 12, a reference gas-exposed electrode 122, a target gas-exposed electrode 121, and a diffused resistance layer 11. The target gas-exposed electrode 121 and the reference gas-exposed electrode 122 are formed on opposed surfaces of the solid electrolyte body 12. The diffused resistance layer 11 is disposed on the surface of the solid electrolyte body 12 so that it is exposed to the gas to be measured which will also be referred to as a target gas below. The diffused resistance layer 11 may alternatively be so disposed as to cover only the target gas-exposed electrode 121.

The adjustment of an output of the gas sensor element 1 is achieved by decreasing the diffusion length of the target gas in the diffused resistance layer 11, i.e., removing a desired thickness $\Delta t$ from each side surface 101 of the gas sensor element 1 perpendicular thereto.

The gas sensor element 1 is, as can be seen from FIG. 1(b), a flat element formed by a lamination of a heater substrate 14 made of, for example, a ceramic material, an insulating spacer 13, the solid electrolyte body 12, and the diffused resistance layer 11. The heater substrate 14 has disposed thereon heater element 140 producing the heat when energized electrically. The insulating spacer 13 has formed therein a reference gas chamber 130 exposed to the atmosphere to introduce thereinto the air as a reference gas. The solid electrolyte body 13 is made of an oxygen ion conductive material such as a ceramic material and has, as described above, the electrodes 121 and 122 formed on the opposed surfaces thereof. The diffused resistance layer 11 is formed on the solid electrolyte body 12 so as to cover the whole of the electrode 121 and made of, for example, a ceramic material.

The diffused resistance layer 11 is installed on a gas-exposed portion of the gas sensor element 1 exposed to the target gas to be measured in concentration and consists of a lamination of a dense layer 111 and a porous layer 112. The dense layer 111 is designed not to permit the target gas to pass through it, while the porous layer 112 permits the target gas to pass through it.

Figure 3:
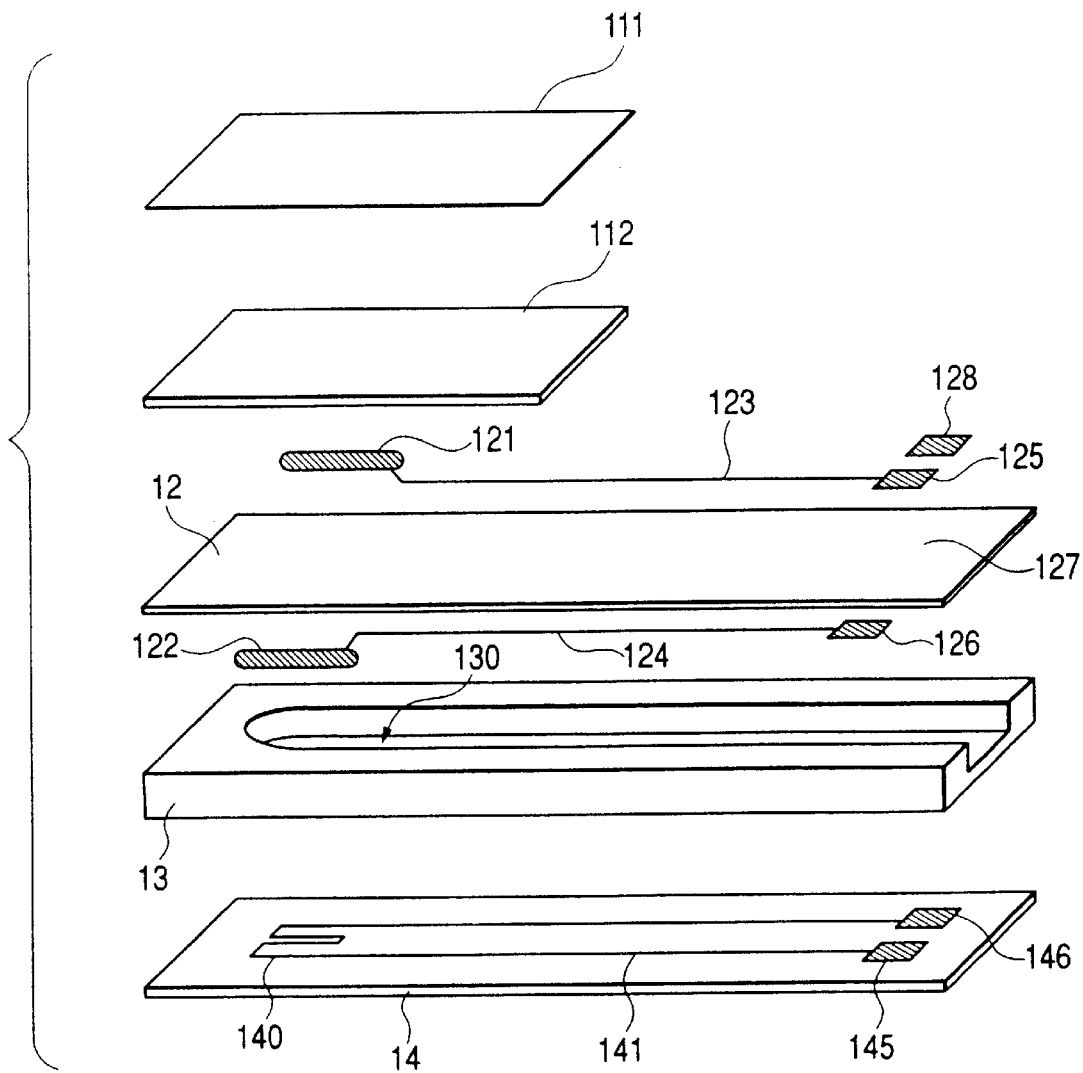
FIG. 3 is an exploded view which shows a gas sensor element.

The heater substrate 14 has disposed thereon, as shown in FIG. 3, the heater element 140, the heater lead 141, and the heater terminals 145 and 146. The heater substrate 14 has also formed on the reverse surface thereof outer terminals (not shown) which electrically connect the heater terminals 145 and 146 to a power supply (not shown), respectively.

The solid electrolyte body 12 has disposed thereon leads 123, 124, an inner terminal 126, outer terminals 125 and 128, and a through hole 127. The lead 123 connects the target gas electrode 121 and the outer terminal 125. The lead 124 connects the reference gas-exposed electrode 122 and the inner terminal 126. The inner terminal 126 electrically connects with the outer terminal 128 through the hole 127. The outer terminals 125 and 128 connect with an external voltage source (not shown). The application of voltage to the outer terminals 125 and 128 will cause the gas sensor element 1 to produce an output current as a function of the concentration of gas.

Figure 2:
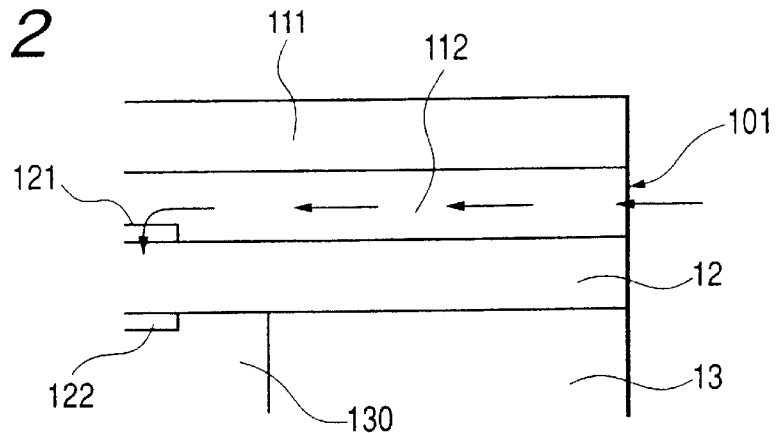
FIG. 2 is a partially vertical sectional view of a gas sensor element.

The path of the target gas diffusing in the gas sensor element 1 is shown in FIG. 2.

The target gas enters the porous layer 112 from the side surface 101 of the gas sensor element 1, moves, as indicated by an arrow, in the porous layer 112, and reaches the target gas-exposed electrode 121. Specifically, the arrow in FIG. 2 indicates the diffusion path. The distance between the side surface 101 and the surface of the target gas-exposed electrode 121 corresponds to the diffusion length.

The decreasing the diffusion length will cause the output of the gas sensor element 1 to be increased.

The adjustment of the output of the gas sensor element 1 is, as described above, by removing the desired thickness Δt from each of the side walls 101 of the gas sensor element 1, i.e., sides of the heater substrate 14, the spacer 13, the solid electrolyte body 12, and the diffused resistance layer 11 from a direction perpendicular to the side walls 101. This removal is achieved by machining, as shown in FIGS. 1(a) and 1(b), only side portions of the gas sensor element 1 having disposed therein the diffused resistance layer 11 using a grinding stone made of diamond powder. In order to avoid breakage of the gas sensor element 1 during the grinding or use, a front portion of the gas sensor element 1 in which the diffused resistance layer 11 is disposed near the boundary 190 between the front portion and a rear portion of the gas sensor element 1 which has no diffused resistance layer is tapered. The removal of the side portions of the gas sensor element 1 may alternatively be accomplished using a laser or chemical etching techniques.

If a desired degree to which the output of the gas sensor element 1 is to be adjusted is not great, only one of the side surfaces 101 of the gas sensor element 1 may be removed.

The production method of the gas sensor element 1 will be described below.

First, a heater substrate sheet, a spacer preform, a solid electrolyte body sheet, a porous layer sheet, and a shielding layer sheet are made using ceramic material and binder.

On the heater substrate sheet, the heater element 140, the heater leads 141, the terminals 145 and 146, and the outer terminals (not shown) which are to be connected to the power supply are, as shown in FIG. 3, printed. On the solid electrolyte body sheet, the electrodes 121 and 122, the leads 123 and 124, and the terminals 125, 126, and 128 are printed. Subsequently, the heater substrate sheet, the spacer preform, the solid electrolyte body sheet, the porous layer sheet, and the shielding layer sheet are pressed to form a lamination.

The thus formed lamination is baked within a furnace heated according to a given temperature profile to make the gas sensor element 1.

Finally, an output of the gas sensor element 1 is adjusted in the following manner.

The gas sensor element 1 is first connected to a check circuit. The voltage is applied to the target gas-exposed electrode 121 and the reference gas-exposed electrode 122 while exposing them to a gas having a selected oxygen concentration. An output current of the gas sensor element 1 is measured and compared with a map listing the relation between a ground amount (i.e., a removed thickness) and a current change to determine the thickness of each side of the gas sensor element 1 to be removed, for example, in unit of millimeter.

Finally, each side of the gas sensor element 1 is machined using a grinding stone made of diamond powder to remove the determined thickness therefrom so as to bring the output of the gas sensor element 1 into agreement with a target value.

A method of making the above map will be discussed below.

First, a test piece of the gas sensor element 1 is prepared. A change in output current is measured while grinding each of the side walls 101 of the test piece.

Figure 4:
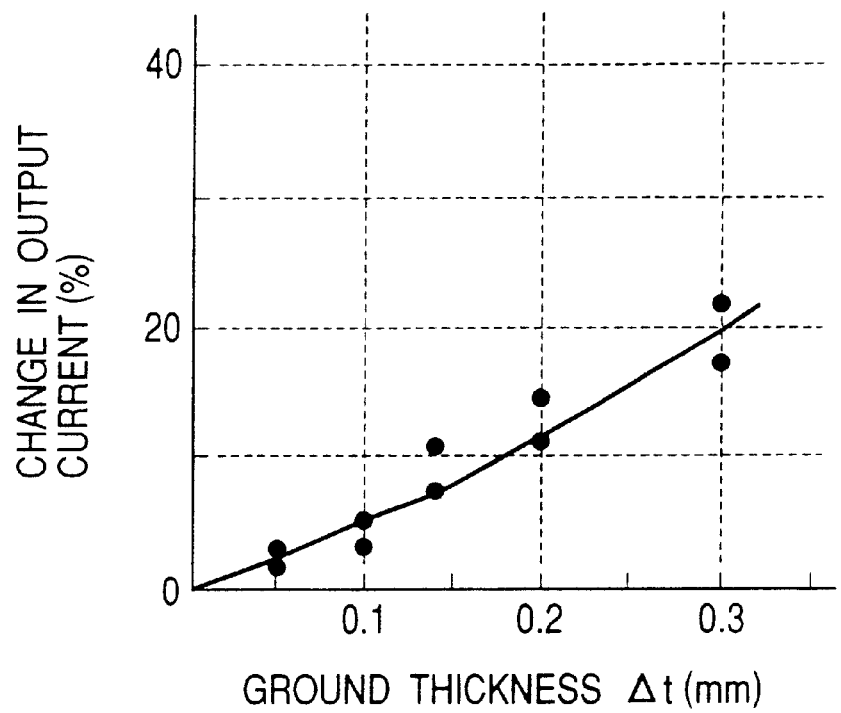
FIG. 4 is a graph which shows the relation of a removed thickness of a gas sensor element and a corresponding output current.

The output current is the current measured when a given voltage is applied to the electrodes 121 and 122. The output of the gas sensor element 1 measured when no voltage is applied is defined as a reference output. The removed thickness Δt of each side surface 101 and a corresponding change in output current are plotted to make the map, as shown in FIG. 4.

The operation of the gas sensor element 1 will be discussed below.

The application of a given voltage to the target gas-exposed electrode 121 and the reference gas-exposed electrode 122 causes the current to flow through the electrodes 121 and 122. The current is determined as a function of the number of oxygen molecules passing through the diffused resistance layer 11.

The diffusion length of the target gas in the diffused resistance layer 11, as shown in FIG. 2, corresponds to the length of a path extending from each side surface 101 to the target gas-exposed electrode 121. The decreasing the diffusion length is, therefore, achieved by only removing the thickness Δt from each side surface 101, thereby resulting in an increase in output current flowing through the electrodes 121 and 122.

Figure 5:
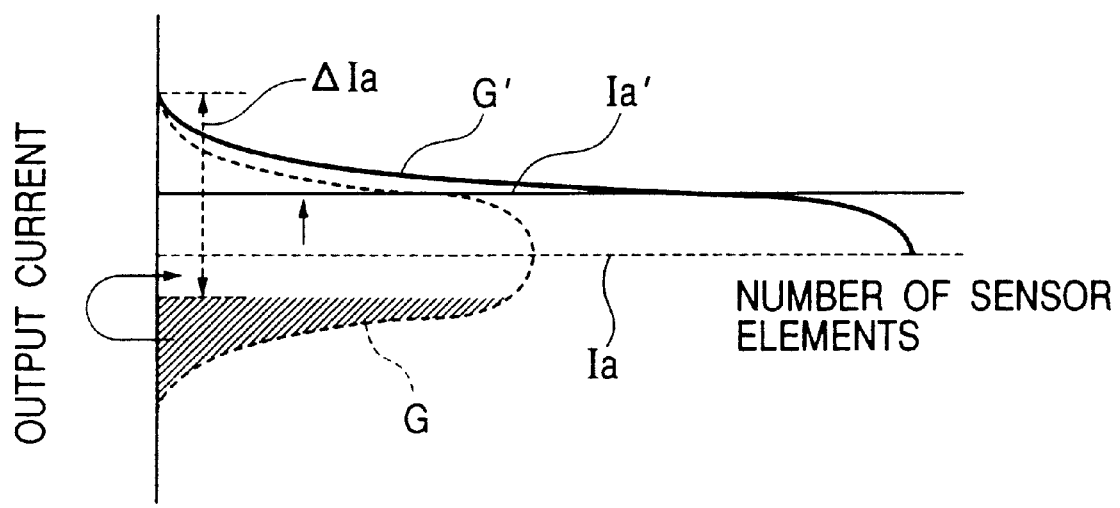
FIG. 5 is a graph which shows a variation in output current of mass-produced gas sensor elements.

In a case where the voltage Vis applied to a plurality of mass-produced sensor elements 1 when the concentration of oxygen contained in the target gas is a, and the distribution of output currents, as represented by G in FIG. 5, is derived which spreads across Ia over an allowable measurement range ΔIa, side surfaces of some of the sensor elements 1 which produce current outputs within a range, as indicated by hatched lines, are ground by the thickness Δt to decrease the diffusion length. This causes the distribution of current outputs thereof to be changed so as to spread, as represented by G', across Ia', thus resulting in a variation in current outputs of the sensor elements 1 falling within the allowable measurement range ΔIa. Specifically, this adjustment absorbs a unit-to-unit variation of the mass-produced sensor elements 1, thereby enabling production of the sensor elements 1 having desired output characteristics at low costs.

The output adjusting method according to the second embodiment will be described below with reference to FIGS. 6 to 9.

Figure 6:
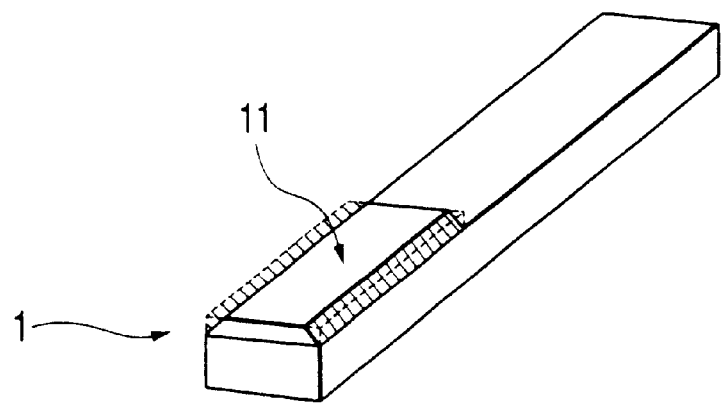
FIG. 6 is a perspective view which shows a gas sensor element whose output is adjusted by a method according to the second embodiment of the invention.
Figure 7:
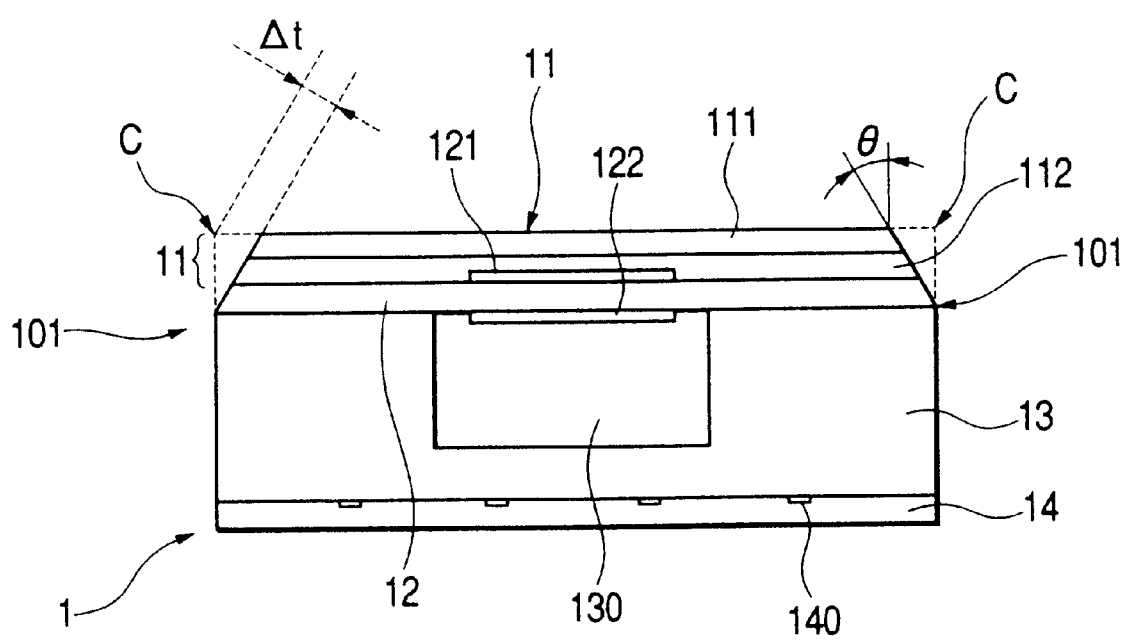
FIG. 7 is a vertical sectional view of FIG. 6.

In this embodiment, the decreasing the diffusion length of the diffused resistance layer 11 for adjusting the output of the gas sensor element 1 is, as shown in FIGS. 6 and 7, accomplished by chamfering the corner C of each of the side surfaces 101 of the diffused resistance layer 11 so that each of the chamfered side surfaces 101 may make angle θ with those before being chamfered (i.e., the side surfaces 101 of the insulating spacer 13). A maximum thickness of a removed portion of each side surface 101 is Δt. If it is not required to adjust the output of the gas sensor element 1 greatly, only one of the side surfaces 101 of the gas sensor element 1 may be removed.

Figure 8:
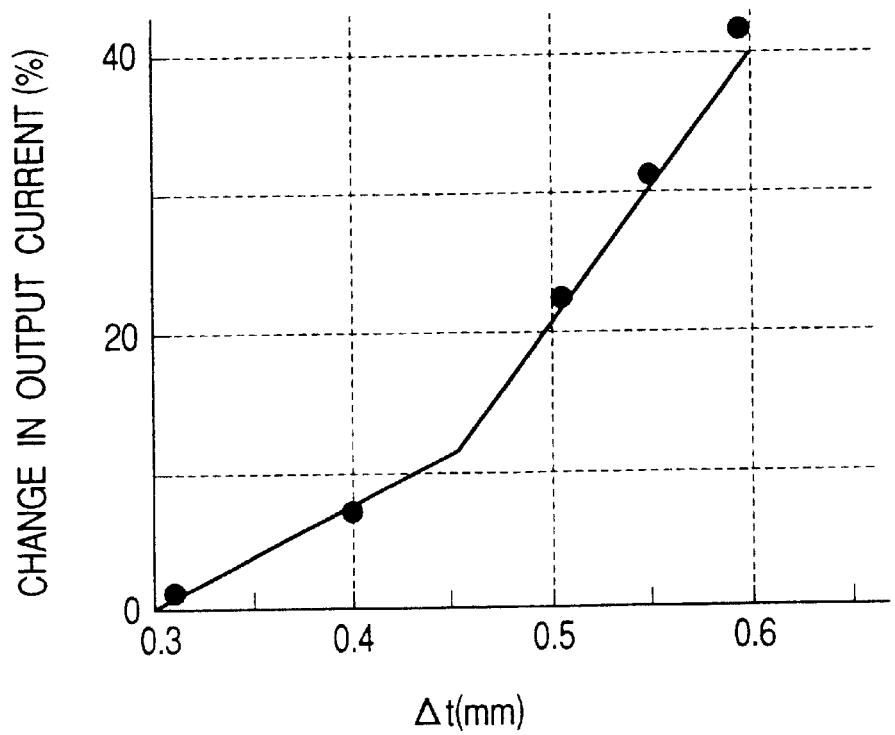
FIG. 8 is a graph which shows the relation of a removed thickness of a gas sensor element and a corresponding output current in the second embodiment.

FIG. 8 represents the relation between the removed thickness Δt of each side surface 101 and a corresponding change in output current of the gas sensor element 1 measured in a similar manner to that as discussed in FIG. 4. It is found that the thickness Δt may be selected from a range of 0 to 0.6 mm and that the output current of the gas sensor element 1 is changed as much as 40% by removing the side surfaces 101 by 0.6 mm. Specifically, the chamfering of the side surfaces 101 of the diffused resistance layer 11 enables the adjustment of the output of the gas sensor element 1 in a wide range and also results in a great decrease in volume of the diffused resistance layer 11 to shorten the diffusion length of the target gas in the diffused resistance layer 11 more greatly, thereby enabling production of the high-response gas sensor element 1.

Figure 9:
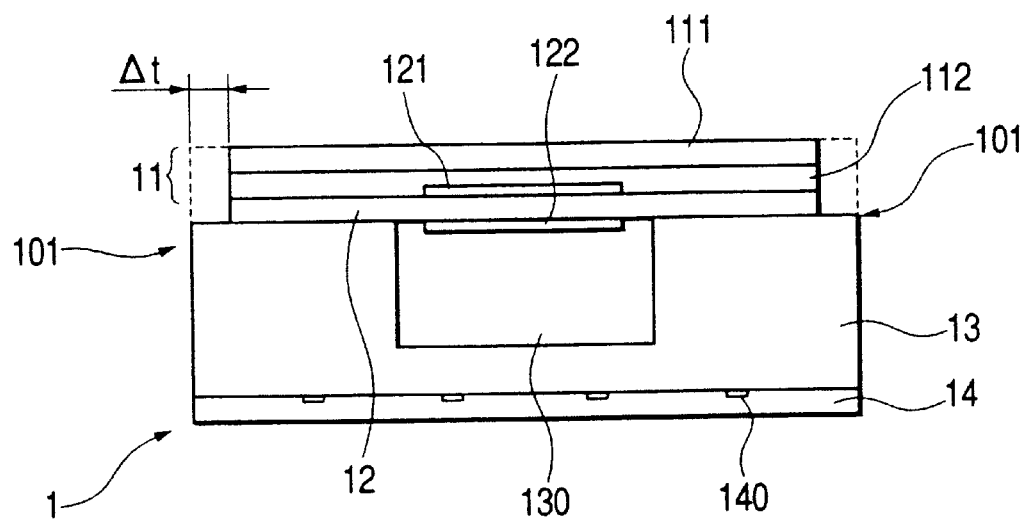
FIG. 9 is a vertical sectional view which shows a gas sensor element whose output is adjusted by a modification of the second embodiment.

The decreasing the diffusion length of the diffused resistance layer 11 may alternatively be, as shown in FIG. 9, accomplished by grinding the side surfaces 101 of only the diffused resistance layer 11 perpendicular thereto by the thickness Δt. If it is not required to adjust the output of the gas sensor element 1 greatly, only one of the side surfaces 101 of the gas sensor element 1 may be removed.

Figure 10:
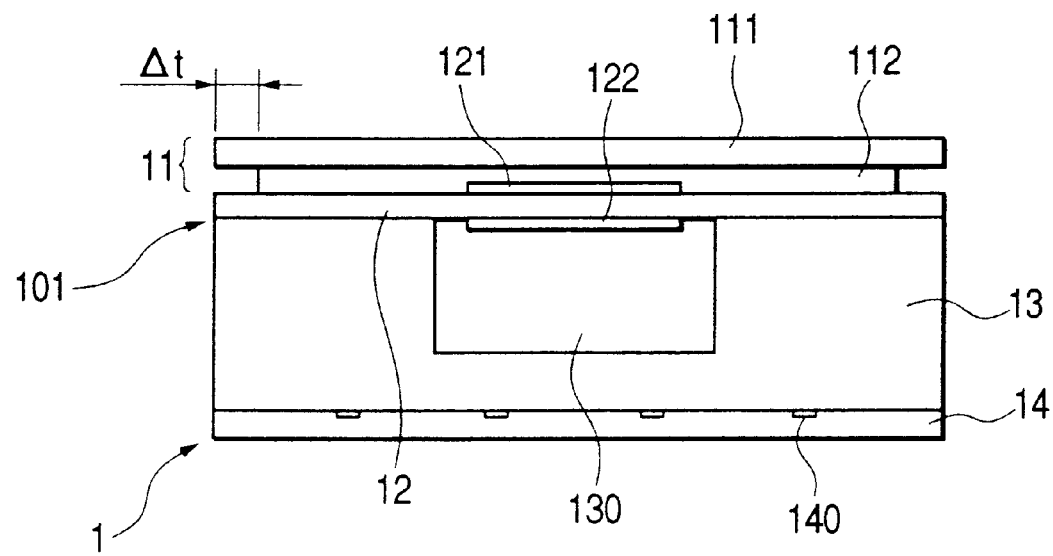
FIG. 10 is a vertical sectional view which shows a gas sensor element whose output is adjusted by a method according to the third embodiment of the invention.

The output adjusting method according to the third embodiment will be described below with reference to FIG. 10.

In this embodiment, the decreasing the diffusion length of the diffused resistance layer 11 is accomplished by grinding the side surfaces 101 of only the porous layer 112 perpendicular thereto by the thickness Δt. If it is not required to adjust the output of the gas sensor element 1 greatly, only one of the side surfaces 101 of the gas sensor element 1 may be removed.

Figure 11:
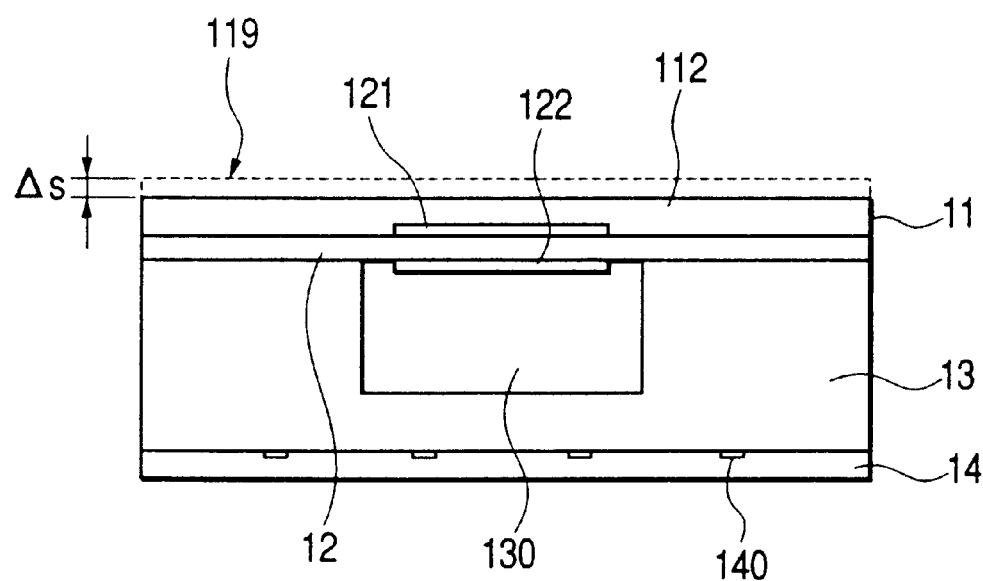
FIG. 11 is a vertical sectional view which shows a gas sensor element whose output is adjusted by a method according to the fourth embodiment of the invention.

The output adjusting method according to the fourth embodiment will be described below with reference to FIG. 11.

The diffused resistance layer 11 of the sensor element in this embodiment consists only of the porous layer 112. The target gas, therefore, diffuses from the upper surface 119 of the porous layer 112 to the target gas-exposed electrode 121. Accordingly, the decreasing the diffusion length of the diffused resistance layer 11 for adjusting the output of the gas sensor element 11 is achieved by grinding the porous layer 112 in a thickness-wise direction thereof, that is, in parallel to the upper surface 119.

The output adjusting method according to the fifth embodiment will be described below with reference to FIGS. 12(a) to 13(b).

The decreasing the diffusion length is achieved by removing the part of the dense layer 111 of the diffused resistance layer 11.

Figure 12A:
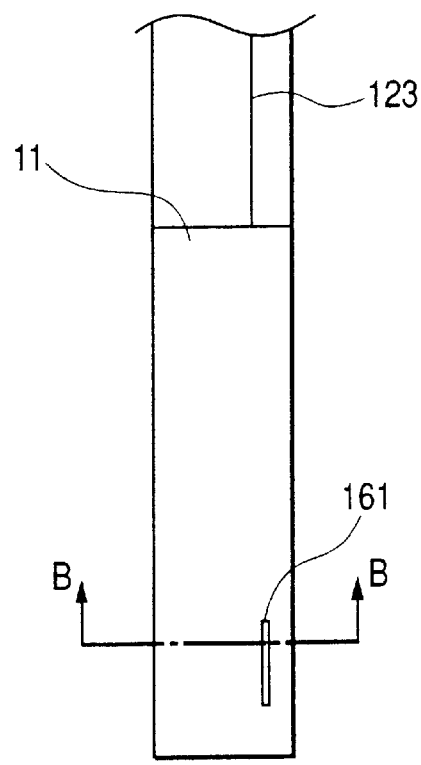
FIG. 12(a) is a partially plan view which shows a gas sensor element whose output is adjusted by a method according to the fifth embodiment of the invention.
Figure 12B:
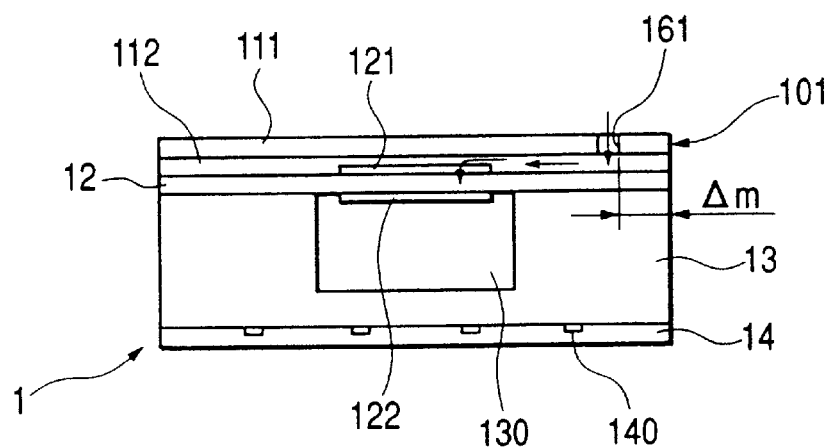
FIG. 12(b) is a vertical sectional view of FIG. 12(a)

Specifically, the rectangular window 161 is, as clearly shown in FIGS. 12(a) and 12(b), formed in the dense layer 111 which reaches the porous layer 112. The window 161 works to introduce the target gas, as indicated by an arrow in FIG. 12(b), to the porous layer 112, thereby decreasing the diffusion length by a distance Δm between the side surface 101 of the gas sensor element 1 and the window 161.

Figure 13A:
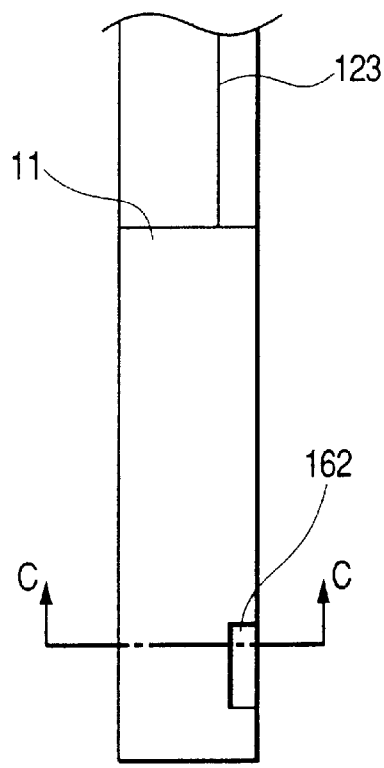
FIG. 13(a) is a partially plan view which shows a gas sensor element whose output is adjusted by a method according to a modification of the fifth embodiment of the invention.
Figure 13B:
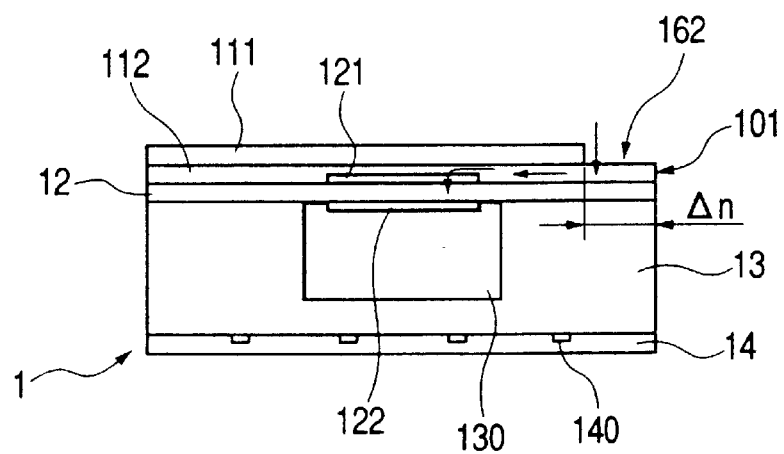
FIG. 13(b) is a vertical sectional view of FIG. 13(a)

The cut-away portion 162, as shown in FIGS. 13(a) and 13(b), may alternatively be formed in the dense layer 111 which reaches the porous layer 112. The cut-away portion 162 introduces the target gas, as indicated by an arrow in FIG. 13(b), to the porous layer 112, thereby decreasing the diffusion length by a distance Δn between the side surface 101 of the gas sensor element 1 and the cut-away portion 162.

Figure 14A:
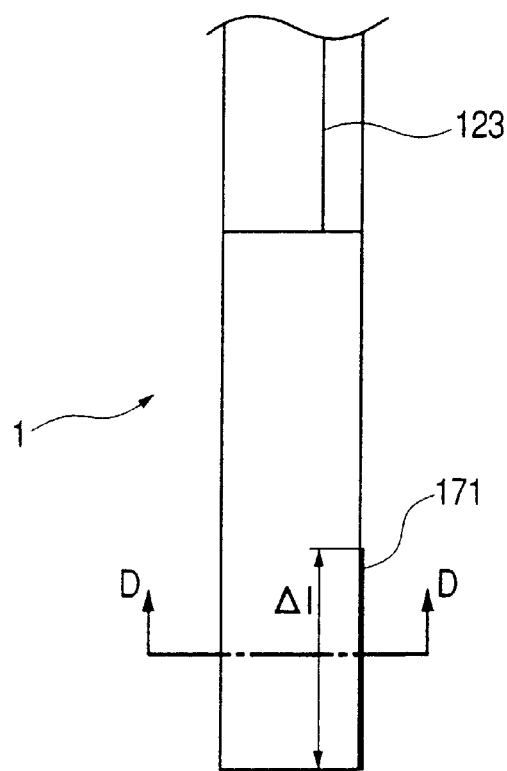
FIG. 14(a) is a partially plan view which shows a sensor element according to the sixth embodiment of the invention.
Figure 14B:
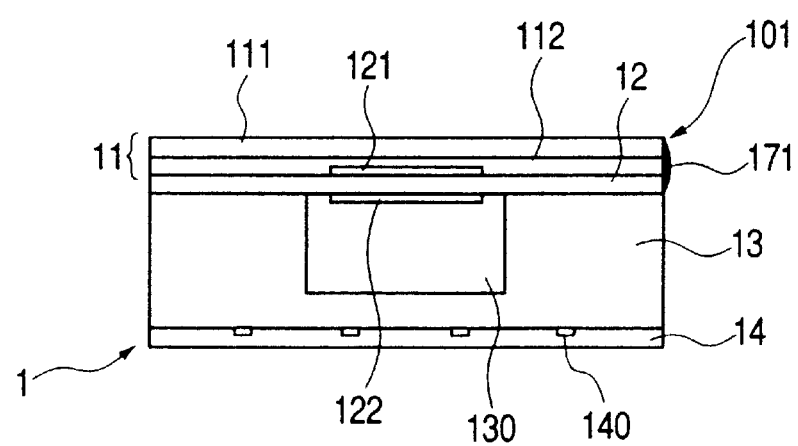
FIG. 14(b) is a vertical sectional view of FIG. 14(a)

The output adjusting method according to the sixth embodiment will be described below with reference to FIGS. 14(a) and 14(b).

Decreasing the diffusion length in this embodiment is achieved by decreasing a side area of the diffused resistance layer 11 at which the target gas enters.

Specifically, the shielding member 171 is installed on one of the side surfaces 101 to decrease the side area of the diffused resistance layer 11 (i.e., the porous layer 112), thereby decreasing a sectional area of the diffused resistance layer 11 within which the target gas diffuses, resulting in a decrease in volume of the target gas entering the diffused resistance layer 11 to decrease the output current of the gas sensor element 1.

The length Δl of the shielding portion 171 is determined as a function of a desired quantity of output current of the gas sensor element 1 to be adjusted. The shielding portion 171 is made of a crystal glass which prohibits the penetration of the target gas and which has preferably a coefficient of thermal expansion close to that of the porous layer 112 in order to avoid generation of thermal stress.

The shielding member 171 may be installed on each of the side surfaces 101.

Figure 15A:
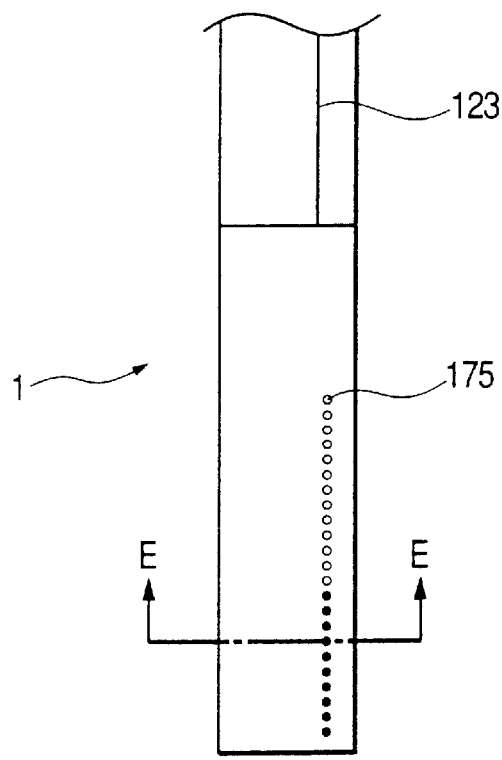
FIG. 15(a) is a partially plan view which shows a sensor element according to the seventh embodiment of the invention.
Figure 15B:
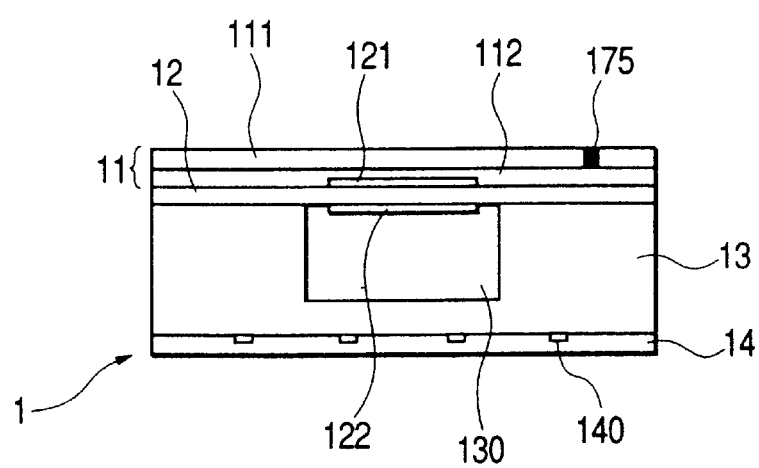
FIG. 15(b) is a vertical sectional view of FIG. 15(a)
Figure 16:
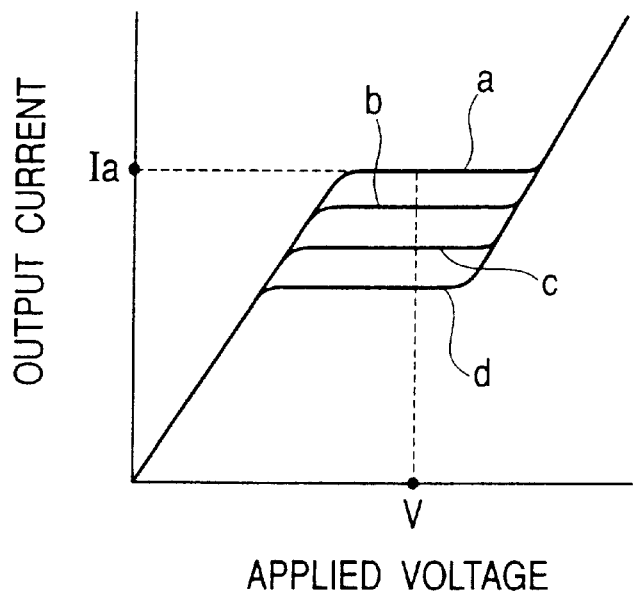
FIG. 16 is a graph which shows the relation between the voltage applied to a target gas-exposed electrode and a reference gas-exposed electrode of a conventional gas sensor element and the current output picked up from the electrodes for difference concentrations a to d of oxygen (a>b>c>d)
Figure 17:
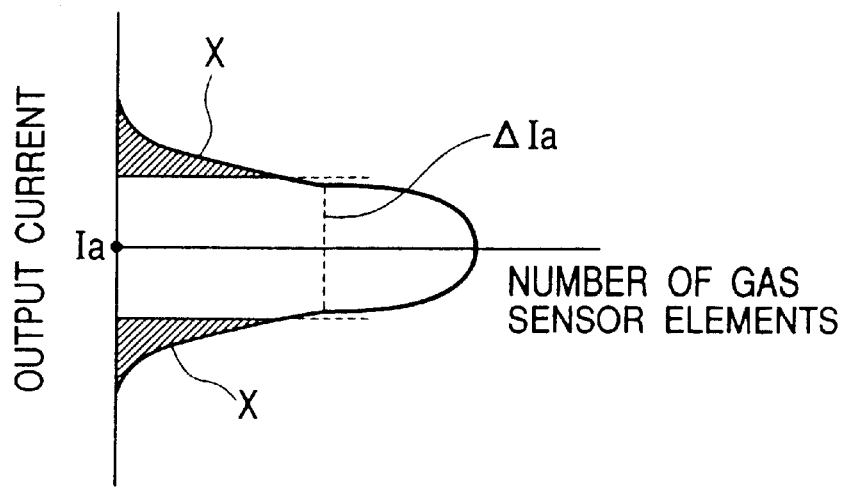
FIG. 17 is a graph which shows a variation in output current of mass-produced conventional gas sensor elements.

The output adjusting method according to the seventh embodiment will be described below with reference to FIGS. 15(a) and 15(b).

Decreasing the diffusion length in this embodiment is, like the sixth embodiment, achieved by decreasing a sectional area of the diffused resistance layer 11.

Specifically, an array of output adjusting holes 175 are formed in the dense layer 111 which lead to the porous layer 112. A desired number of the output adjusting holes 175 are sealed with a crystal glass which prohibits the penetration of the target gas.

If all the output adjusting holes 175 are not sealed, the gas-diffused sectional area of the gas sensor element 1 within which the target gas diffuses corresponds to the sum of an area of the porous layer 112 facing the target gas and a total sectional area of the output adjusting holes 175. Therefore, if one of the output adjusting holes 175 is closed, the gas-diffused sectional area of the gas sensor element 1 is decreased by the sectional area of the one output adjusting hole 175. The number of the output adjusting holes 175 to be closed is determined as a function of the quantity of output current to be adjusted.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A gas sensor output adjusting method comprising:

preparing a gas sensor element including lamination of a solid electrolyte body, a target gas-exposed electrode, a reference gas-exposed electrode, and a diffusion resistance layer in which a target gas to be measured diffuses, the target gas-exposed electrode being disposed on a first surface of the solid electrolyte body to be exposed to the target gas, the reference gas-exposed electrode being disposed on a second surface of the solid electrolyte body to be exposed to a reference gas, the diffusion resistance layer having an outer surface to be exposed to the target gas, an inner surface opposite the outer surface, disposed on the first surface of the solid electrolyte body, and side surfaces formed between the outer and inner surfaces, defining portions of side surfaces of the lamination, the target gas-exposed electrode and the reference gas-exposed electrode producing a current output as a function of target gas concentration;

exposing the target gas-exposed electrode to a predetermined concentration of target gas and exposing the reference gas-exposed electrode to reference gas;

measuring the current output produced from the target gas-exposed electrode and the reference gas-exposed electrode; and decreasing diffusion length of the target gas in the diffusion resistance layer as a function of the measured current output by removing a portion of the diffusion resistance layer obliquely to at least one of the side surfaces of the lamination for adjusting the current output to a predetermined value corresponding to the predetermined target gas concentration.

2. A gas sensor output adjusting method as in claim 1, wherein said decreasing step chamfers a corner of the at least one side surface of the lamination.

3. A gas sensor output adjusting method as in claim 1, wherein the diffusion resistance layer includes a porous layer disposed on the first surface of the solid electrolyte body and a dense layer which is disposed on the porous layer and which dense layer substantially impedes target gas from passing therethrough.

4. A gas sensor output adjusting method comprising:

preparing a laminated gas sensor element having a diffusion resistance layer having top and side surfaces;

exposing the gas sensor element to a predetermined concentration of target and to a reference gas and measuring a current output therefrom under such conditions; and decreasing a diffusion path length for the target gas in said diffusion resistance layer as a function of said measured current output by removing a portion of the diffusion resistance layer along an edge corner of said diffusion resistance layer that intersects obliquely with said top and side surfaces of the diffusion resistance layer thereby adjusting the current output to a predetermined value corresponding to the predetermined target gas concentration.

5. A gas sensor output adjusting method as in claim 4 wherein said step of decreasing chamfers a corner of at least one top side surface of the diffusion resistance layer.

6. A gas sensor output adjusting method as in claim 4 wherein the diffusion resistance layer includes a porous layer disposed on the surface of a solid electrolyte body and a dense layer disposed on the porous layer and which dense layer substantially impedes target gas from passing therethrough.

* * * * *